US010544921B2

(12) United States Patent
Li

(10) Patent No.: US 10,544,921 B2
(45) Date of Patent: Jan. 28, 2020

(54) LUMINAIRE WITH INDEPENDENTLY-CONTROLLABLE FOCUS-TUNABLE LENSES

(71) Applicant: Excelitas Technologies Corp., Waltham, MA (US)

(72) Inventor: Wei Li, South Barrington, IL (US)

(73) Assignee: Excelitas Technologies Corp., Waltham, MA (US)

(*) Notice: Subject to any disclaimer, the term of this patent is extended or adjusted under 35 U.S.C. 154(b) by 242 days.

(21) Appl. No.: 15/584,318

(22) Filed: May 2, 2017

(65) Prior Publication Data

US 2018/0320860 A1 Nov. 8, 2018

(51) Int. Cl.
| | |
|---|---|
| F21V 14/00 | (2018.01) |
| F21V 5/04 | (2006.01) |
| F21V 23/04 | (2006.01) |
| A61B 90/30 | (2016.01) |
| F21W 131/20 | (2006.01) |
| F21V 7/06 | (2006.01) |

(52) U.S. Cl.
CPC ............ *F21V 14/003* (2013.01); *A61B 90/30* (2016.02); *F21V 5/04* (2013.01); *F21V 14/00* (2013.01); *F21V 23/0471* (2013.01); *F21V 7/06* (2013.01); *F21W 2131/20* (2013.01)

(58) Field of Classification Search
CPC ..... F21V 14/003; F21V 14/00; F21V 23/0471
See application file for complete search history.

(56) References Cited

U.S. PATENT DOCUMENTS

| | | | |
|---|---|---|---|
| 4,288,844 A | 9/1981 | Fisher et al. | |
| 5,067,064 A | 11/1991 | Gehly et al. | |
| 5,774,273 A | 6/1998 | Bornhorst | |
| 6,702,483 B2* | 3/2004 | Tsuboi | G02B 3/14 |
| | | | 348/E5.04 |
| 8,408,745 B2 | 4/2013 | Cameron et al. | |
| 8,944,647 B2 | 2/2015 | Bueeler et al. | |
| 9,470,405 B2 | 10/2016 | Boccoleri et al. | |
| 2003/0185009 A1 | 10/2003 | Walters | |

(Continued)

FOREIGN PATENT DOCUMENTS

| | | |
|---|---|---|
| DE | 10005795 A1 | 8/2001 |
| EP | 1568937 A1 | 8/2005 |

(Continued)

OTHER PUBLICATIONS

Machine translation of Ladstatter, Gerald, EP 2302295A1, published Mar. 30, 2011 (Year: 2011).*

(Continued)

*Primary Examiner* — William N Harris
(74) *Attorney, Agent, or Firm* — Peter A. Nieves; Sheehan Phinney Bass & Green PA

(57) ABSTRACT

A luminaire includes multiple light emitting cells. Each light emitting cell has a light source, and a focus-tunable lens (e.g., a liquid lens) associated with the light source. Each respective one of the light emitting cells is independently controllable relative to the one or more other light emitting cells. In a typical implementation, the control of each light emitting cell may involve, for example, controlling a surface of liquid in the corresponding liquid lens.

10 Claims, 12 Drawing Sheets

(56) References Cited

U.S. PATENT DOCUMENTS

| | | | |
|---|---|---|---|
| 2006/0176574 A1* | 8/2006 | Tukker | G02B 3/14 |
| | | | 359/665 |
| 2008/0252990 A1* | 10/2008 | Onuki | G02B 3/14 |
| | | | 359/666 |
| 2009/0122388 A1* | 5/2009 | Kuiper | G02B 5/1828 |
| | | | 359/295 |
| 2009/0252485 A1* | 10/2009 | Tsuchiya | G02B 3/0037 |
| | | | 396/200 |
| 2009/0296408 A1 | 12/2009 | Hendrikus | |
| 2011/0051425 A1* | 3/2011 | Tsuchiya | F21V 5/04 |
| | | | 362/296 |
| 2013/0121005 A1 | 5/2013 | Dahmen | |
| 2015/0252984 A1* | 9/2015 | Van Bommel | F21V 14/00 |
| | | | 362/84 |
| 2016/0174336 A1 | 6/2016 | Elfring | |

FOREIGN PATENT DOCUMENTS

| | | |
|---|---|---|
| EP | 2302295 A1 | 3/2011 |
| JP | 2008145905 A | 6/2008 |

OTHER PUBLICATIONS

Machine translation of Marka, Rudolf, EP 1568937A1, published Aug. 31, 2005 (Year: 2005).*
Optotune; Focus tunable lenses; http://www.optotune.com/technology/focus-tunable-lenses; downloaded from internet Apr. 4, 2017.
Varioptic Dynamic Lens; Liquid lens Applications; Invenios France SAS; downloaded from the Internet Apr. 4, 2017.
International Search Report and Written Opinion for PCT/US2017/030536 dated Jun. 8, 2017.

* cited by examiner

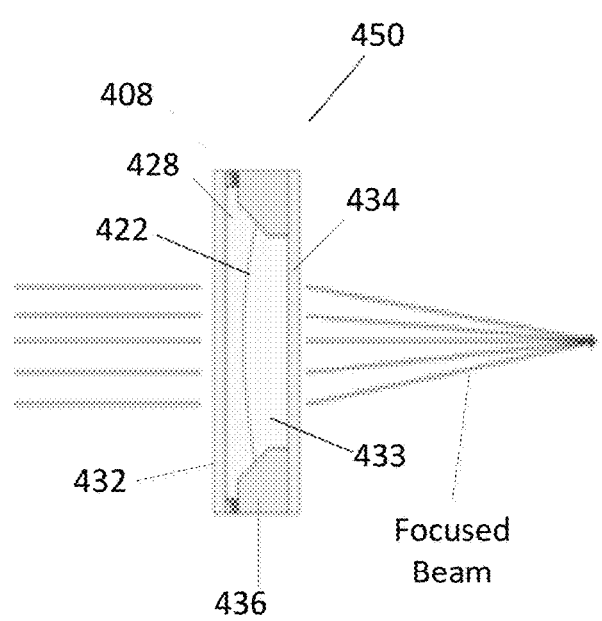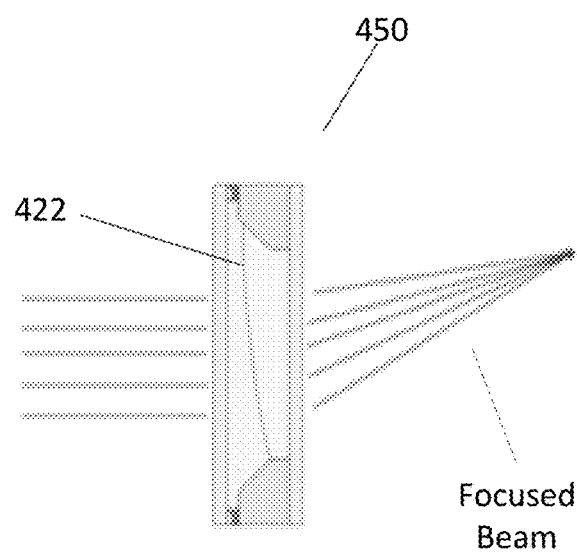
FIG. 4A
FIG. 4B

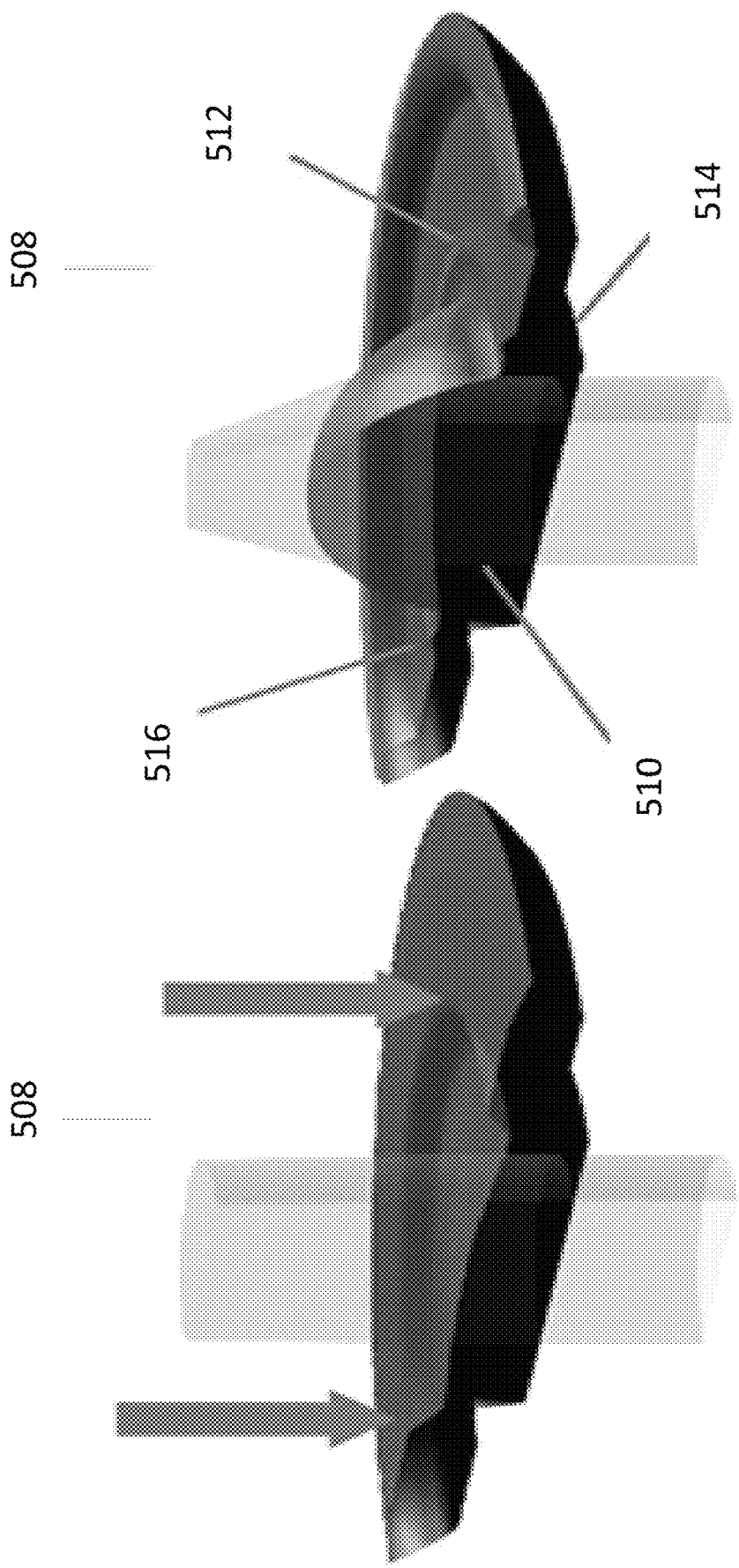

LUMINAIRE WITH INDEPENDENTLY-CONTROLLABLE FOCUS-TUNABLE LENSES

FIELD OF THE INVENTION

This disclosure relates to luminaires and, more particularly, relates to luminaires with independently-controllable focus-tunable lenses (e.g., liquid lenses).

BACKGROUND

A luminaire is a lighting device that is adapted to provide illumination to a particular area. There are a variety of specific uses for luminaires including, for example, in medical settings (e.g., examination rooms, operating rooms, dental offices, etc.). It is critical that areas such as these, and others, are properly illuminated during various procedures and/or periods of time.

SUMMARY OF THE INVENTION

In one aspect, a luminaire includes multiple light emitting cells. Each light emitting cell has a light source, and a focus-tunable lens (e.g., a liquid lens) associated with the light source. Each respective one of the light emitting cells is independently controllable relative to the one or more other light emitting cells. In a typical implementation, the control of each light emitting cell may involve, for example, controlling a surface of liquid in the corresponding liquid lens.

In another aspect, a lighting module (e.g., that may be used in the luminaire mentioned above, for example) includes a printed circuit board, and two or more light emitting cells coupled to the printed circuit board. Each of the two or more light emitting cells may have: a light source, and a focus-tunable lens associated with the light source. The printed circuit board is configured to facilitate independent control over each respective one of the light emitting cells relative to the one or more other light emitting cells.

In yet another aspect, a method of delivering light to a site includes providing a luminaire (as mentioned above, for example), and controlling one of the light emitting cells in the apparatus independently from the other lighting emitting cell(s) in the apparatus to adjust the light beam produced by that light emitting cell. More particularly, in a typical implementation, the luminaire includes multiple light emitting cells and each light emitting cell has: a light source, and a focus-tunable lens (e.g., a light lens) associated with the light source. Each respective one of the light emitting cells may be independently controllable relative to the one or more other light emitting cells.

In some implementations, one or more of the following advantages are present.

For example, a luminaire may be produced that offers superb adjustability and adaptability of the light to be delivered thereby. On key advantage of the focus-tunable lenses (e.g., liquid lens) are their ruggedness (no moving parts), fast response times, good optical quality, low power consumption and size.

In a typical implementation, the independent nature of the control of the focus-tunable lenses generally helps to provide a great deal of adaptability in the quality, shape, intensity, and/or size of the light spot being supplied to a particular site from the luminaire. This adaptability can be particularly desirable in applications, such as medical lighting, where the ability to see a particular area with great clarity is highly desirable. Automatic control of each specific light emitting cell may be even better.

Moreover, Industry standard IEC60601 requires the center illuminance at 1 m from a luminaire to be tested, along with light field diameter $D_{10}$. $D_{10}$ is defined as the diameter of a light patch at 10% of center illuminance, also the average of the measured values along four cross-sections through the light filed center. It's highly desired to have a luminaire with light field diameter as small as 150 mm at 1 m, so the light is highly collimated. In the case with multiple light emitting cells within a luminaire, the smallest possible light field diameter (aka spot size) can be achieved with each cell directing light to the same location with smallest size. Certain luminaires disclosed herein are able to achieve this while supporting each light emitting cell so that its axis parallel to luminaire axis and the luminaire base is planar.

Other features and advantages will be apparent from the description and drawings, and from the claims.

BRIEF DESCRIPTION OF THE DRAWINGS

FIGS. 4A and 4B are side views showing an exemplary focus-tunable lens, which in the illustrated implementation is a liquid lens, in two operational states.

FIGS. 5A and 5B are side views showing an alternative example of an exemplary focus-tunable lens in two operational states.

In the drawings, similar like numerals refer to like elements.

DETAILED DESCRIPTION

Figure 1:
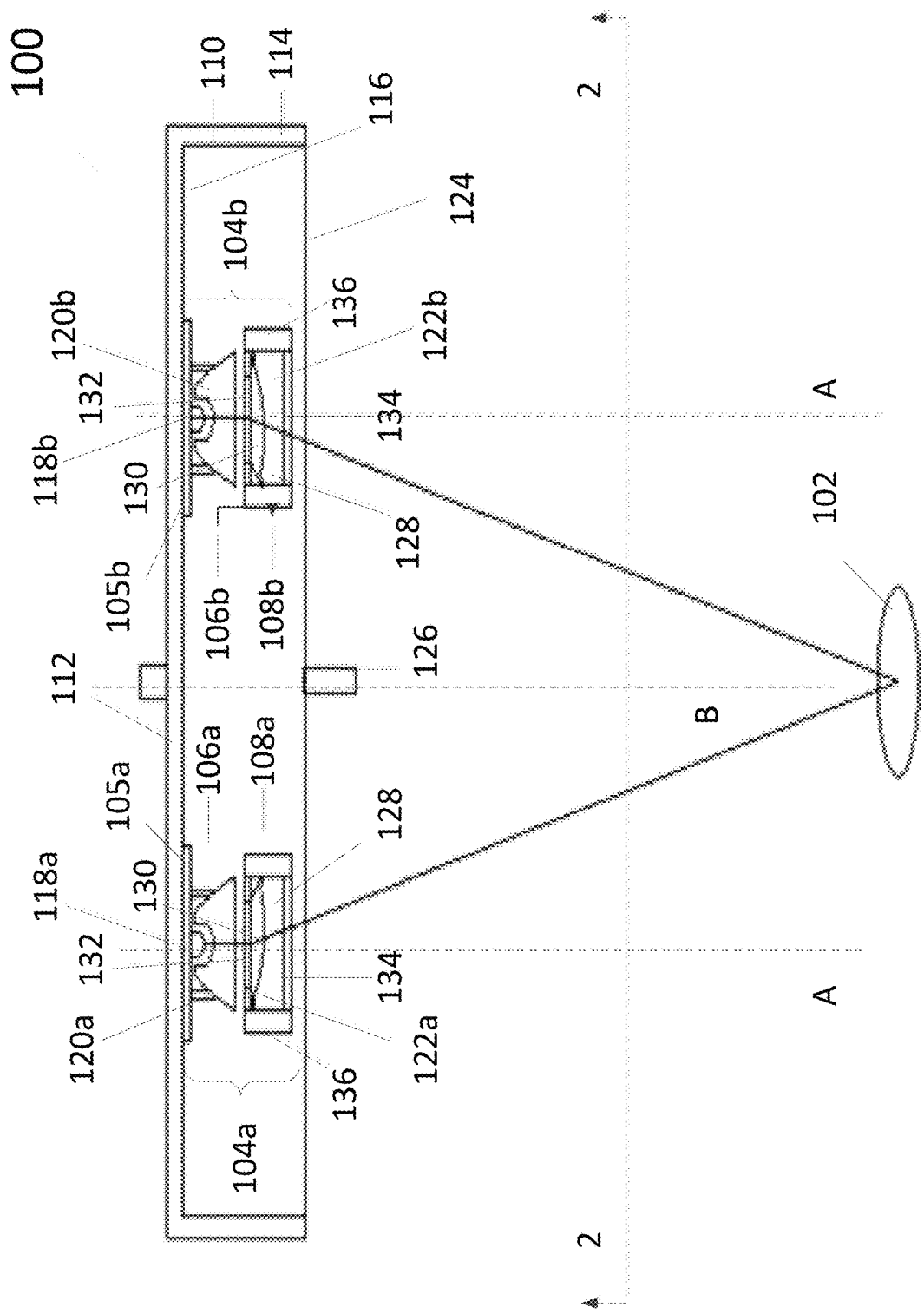
FIG. 1 is a cross-sectional, schematic, side view of an exemplary luminaire and shows how light that is emitted from the luminaire can be directed onto a site below the luminaire.

FIG. 1 is a cross-sectional, schematic, side view of a luminaire 100 and showing how light that is emitted from the luminaire 100 can be directed onto a site 102 below the luminaire. The luminaire is particularly well suited for use in connection with applications in the medical industry, such as clinics, operating rooms, dental practices, medical practices, laboratories, etc. Of course, the luminaire could be used in connection with other applications, particularly where adequate lighting is critical or highly desirable.

The illustrated luminaire 100 has multiple light emitting cells (e.g., 104a, 104b). Two (104a, 104b) are shown in the cross-sectional view of FIG. 1. However, FIG. 2 (an alternative view of the luminaire 100 in FIG. 1) shows that there are actually twelve (12) light emitting cells in the luminaire 100. Each light emitting cell (e.g., 104a, 104b) has a printed circuit board 105a, 105b, a light source 106a, 106b physically coupled to the printed circuit board 105a, 105b, and an focus-tunable lens (e.g., a liquid lens 108a, 108b, or the like) associated with each light source 106a, 106b. Generally speaking, in various implementations, the phrase focus-tunable and the like may be construed broadly to include virtually any kind of lens that can be adjusted to change its focus (including, e.g., the direction of light exiting the lens and/or the width of the beam thereby produced, etc.).

In a typical implementation, the printed circuit boards (105a, 105b) are configured to physically support a corresponding light source (106a, 106b) and liquid lens (108a, 108b). Moreover, each printed circuit board (105a, 105b) has at least a substrate, which is substantially flat in the illustrated implementation, and one or more electrically conductors (e.g., electrically conductive traces, vias, etc.) coupled to the substrate and configured to deliver electric energy for use by the corresponding light source (106a, 106b), the corresponding liquid lens (108a, 108b), or both.

The light sources (106a, 106b), which are coupled to the printed circuit boards (105a, 105b), can be virtually any kind of light sources. In the illustrated example, each lights source (106a, 106b) includes a light element (118a, 118b) and an optical element (120a, 120b), also referred to as optic(s). More particularly, in the illustrated example, the light elements (118a, 118b) may be, for example, light emitting diodes, incandescent light bulbs, fluorescent light bulbs, or virtually any other kind of light producing element. The optical element (118a, 118b) in the illustrated implementation is a parabolic reflector. However, this optical element (118a, 118b) can be virtually any one of a variety of different types of optical elements (e.g., a lens, a light guide of any shape, a total internal reflection (TIR) lens, a fiber bundle, an aperture, a diffuser, etc.). In some implementations, this optical element (118a, 118b) can be eliminated entirely.

The liquid lenses (108a, 108b) essentially act as controllable variable focus optical devices. These liquid lenses (108a, 108b) can have any one of a variety of possible configurations. In one exemplary implementation, such as the one represented in FIG. 1, the liquid lenses may have a housing that is filled with two fluids such as water 128 and oil 130 that do not readily mix but that form an interface surface (see, e.g., 122a, 122b in FIG. 1) therebetween. The housing may have two transparent windows that may be glass or plastic, for example, on opposite sides of the fluid container—an inlet window 132 that allows light (e.g., from one of the light sources) to enter the fluid container so that it can pass through (and be influenced by) the oil-water interface surface (122a, 122b), and—an outlet window 134 that allows light to exit the fluid container. The liquid lens may also have provisions (e.g., electrodes 136 coupled to an electric power source, not shown in FIG. 1) that can facilitate creating and/or varying an electromagnetic field that, when exposed to the fluid container, influences the contour of the oil-water interface surface (122a, 122b). Changes in the contour (e.g., radius and/or tilt) of the oil-water interface surface (122a, 122b) can affect the direction, beam size, intensity, etc. of light that passes through the liquid lens. Liquid lenses generally have no moving parts that might wear out due to friction. Therefore, advantageously, liquid lenses tend to have long operating lives.

In the illustrated implementation, each liquid lens (108a, 108b) is coupled to and associated with a corresponding one, and only one, of the light sources (106a, 106b). This association means that the liquid lens (108a, 108b) is positioned near and configured relative to the corresponding light source (106a, 106b) such that a significant amount (e.g., at least 90%) of light from the corresponding light source passes through the liquid lens before reaching the site that is meant to be illuminated (e.g., 102 in FIG. 1). Thus, the direction, beam size, intensity, etc. of the light will be influenced by the contour of the oil-water interface in the liquid lens.

In some exemplary implementations, the focus-tunable lenses (e.g., liquid lenses 108a, 108b in FIG. 1) may be a variable focus liquid lens, such as those available from the Varioptic™ dynamic lens company. In some exemplary implementations, the focus-tunable lenses may be focus-tunable lenses available from the Optotune™ company.

In a typical implementation, each respective one of the light emitting cells (e.g., 104a, 104b) in the luminaire 100 is independently controllable relative to any one or more (or all) of the other light emitting cells in the luminaire 100. This means, for example, in various implementations, either the light source (106a, 106b), the liquid lens (108a, 108b), or both may be controllable in a particular light emitting cell (104a, 104b). Controlling a light source may include, for example, controlling the brightness or color of light being produced by that light source. Controlling a liquid lens may include, for example, controlling the contour of the oil-water interface surface in the liquid lens to control how the light passing through it ends up being influenced. In various implementations, the control may be provided by an external electronic controller, which is not shown or represented in FIG. 1.

In a typical implementation, the independent nature of the control that is exerted over the light emitting cells generally helps to provide a great deal of control and adaptability in the quality, shape, intensity, size, etc. of any light spot(s) (e.g., 102) being supplied to a particular site from the luminaire 100. This adaptability can be desirable in a variety of settings including, notably, applications such as medical lighting where the ability to see a particular area with great clarity is critical or at least highly desirable.

The illustrated luminaire 100 has a housing 110. The housing 110 can be configured in a variety of different ways. In the illustrated implementation, the housing 110 has a substantially flat bottom portion 112, and one or more side walls 114 that extend from the outer perimeter of the bottom portion 112 and surround the light emitting cells (104a, 104b). The bottom portion 112 of the housing 110 defines an inner, substantially flat mounting surface 116 for the light emitting cells (104a, 104b). According to the illustrated implementation, the printed circuit board (105a, 105b) for each light emitting cell (104a, 104b) is rigidly coupled to the substantially flat mounting surface 112 and configured such that an optical axis ("A") of the light emitting cell (104a, 104b) is substantially parallel to an axis ("B") of the overall luminaire 100.

The "optical axis" of a light emitting cell, as used herein, should be understood as referring to an imaginary line that passes through the center of the light emitting cell and that defines a path, along which light propagates at least from the light source to the corresponding liquid lens. In the illustrated implementation, the optical axis ("A") of each light emitting cell is perpendicular to the substantially flat mounting surface 112. The phrase "axis of the overall luminaire," as used herein, should be understood as referring to an imaginary line that passes through the center of the luminaire, about which the luminaire or the luminaire housing is substantially symmetrical. Typically, the axis of the overall luminaire defines a general direction that light would travel, if unaffected by any of the liquid lenses, from the luminaire, toward a surface to be illuminated.

Thus, in a typical implementation, each light emitting cell (104a, 104b) is rigidly coupled to the substantially flat mounting surface 112, has a light source (106a, 106b) that is configured to emit light in a direction that is substantially perpendicular to the substantially flat mounting surface, and the direction, beam size, intensity, etc. of that light can be, and is, influenced by the contours of the oil-water interface surfaces (122a, 122b) in each respective one of the light emitting cells 104a, 104b.

In some implementations, the housing 110 may have a cover 124 that is attached to distal ends of the side wall(s) 114 of the housing 110 and that extends over the light emitting cells (104a, 104b) to protect and contain them. While the housing 110 may be substantially opaque, the cover 124 is typically transparent. The luminaire 100 is physically supported by a mounting structure 126, which can, of course, have any one of several different types of configurations.

In a typical implementation, the luminaire 100 may include or be connected to an external controller (e.g., an electronic controller) that is configured to control the luminaire 100. This controller (not shown in FIG. 1) may enable a human user to manually control the luminaire 100 or to program the luminaire 100 to operate automatically. The control imposed by the controller may include controlling or influencing the contour of the fluid interface surface in the liquid lenses. The control imposed also may include controlling the light sources (e.g., by causing a change in voltage or current being delivered to the light source). Moreover, in a typical implementation, the controller is configured to control each respective one of the multiple light emitting cells (104a, 104b) independently from the other light emitting cells (104a, 104b).

Figure 2:
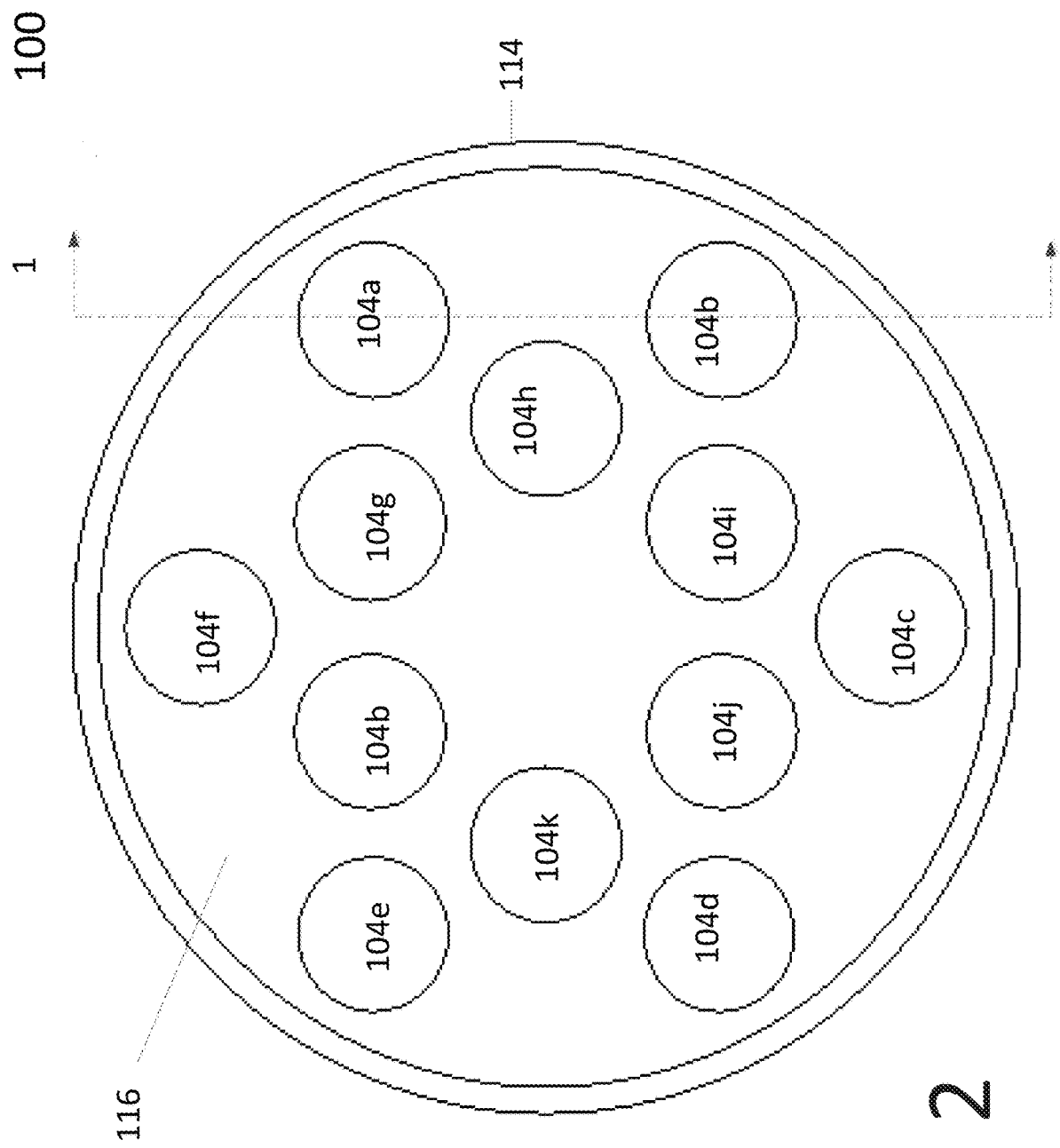
FIG. 2 is an alternative view of the luminaire from FIG. 1, taken along line 2-2 in FIG. 1.

Referring to FIG. 2, the concept of independent control as used herein should be understand to include the possibility that any one or more of the light emitting cells in the illustrated luminaire may be controlled, manipulated or adjusted without controlling, manipulating or adjusting any other light emitting cells in the luminaire. Moreover, the concept of independent control as used herein should be understand to include the possibility that any group of light emitting cells in the luminaire may be controlled, manipulated or adjusted as a group without controlling, manipulating or adjusting any other light emitting cells in the luminaire.

Figure 3A:
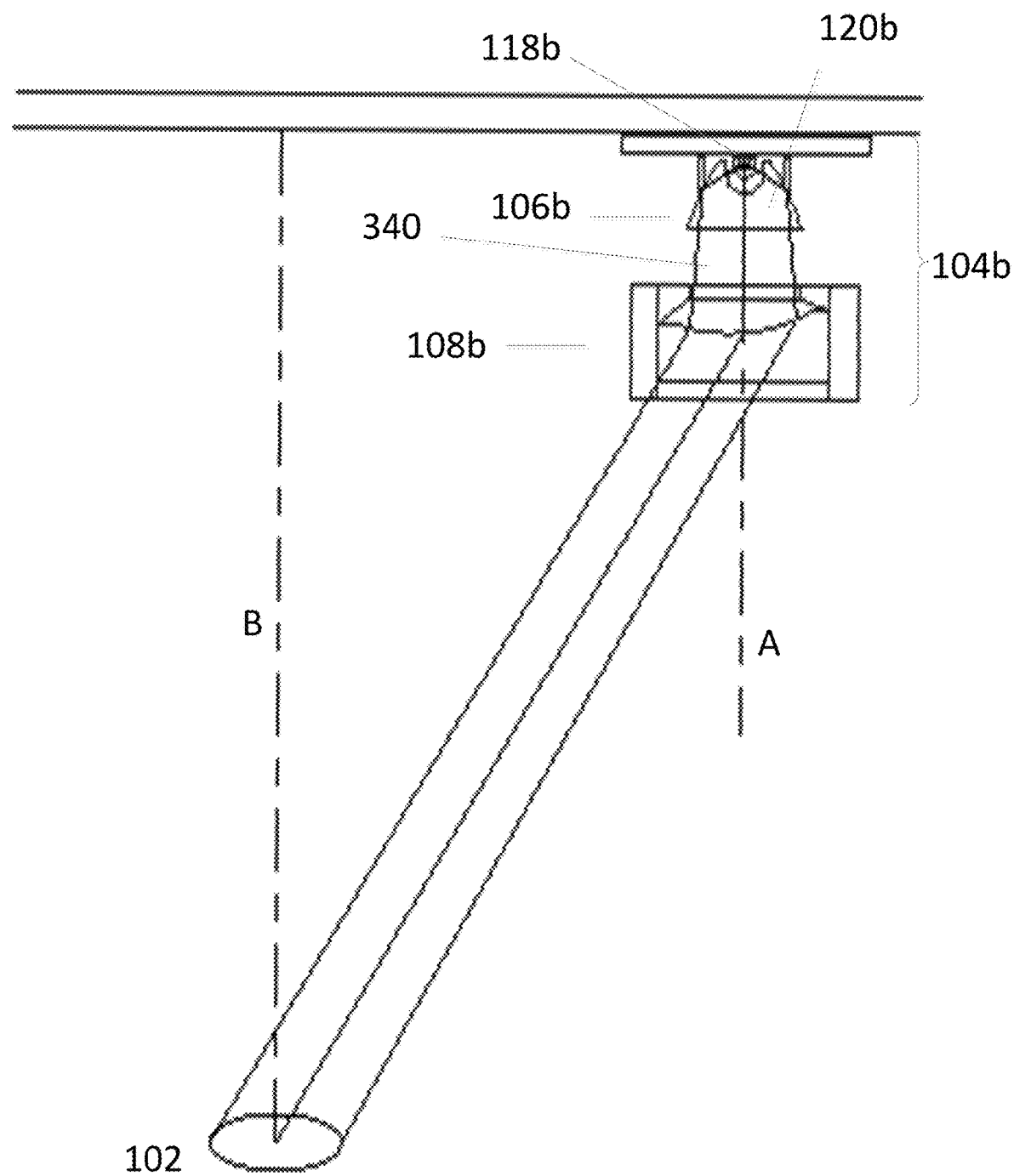
FIGS. 3A-3C are partial cross-sectional, schematic, side views of the luminaire from FIG. 1 showing various ways in which light that is emitted from one of the light emitting cells can be influenced by the liquid lens.

FIG. 3A is a partial cross-sectional, schematic, side view of luminaire 100 showing how light that is emitted from one of the light emitting cells (e.g., 104b) can be influenced by the liquid lens 108b.

The light source 106b of the illustrated light emitting cell 104b is shown to be emitting a light cone 340 in a direction that is substantially perpendicular to the flat mounting surface 116, to which the light emitting cell 104b is mounted. The light cone 340 passes through the liquid lens 108b, where the contour of the oil-water interface surface 122b causes the light cone 340 to bend and exit the liquid lens in a different direction than the direction that the light cone 340 entered the liquid lens 108b. Thus, in FIG. 3A, the liquid lens 108b changes the direction of the beam spot. This represents one exemplary manner in which a liquid lens may influence light from a corresponding one of the light emitting cells in a particular luminaire.

Figure 3B:
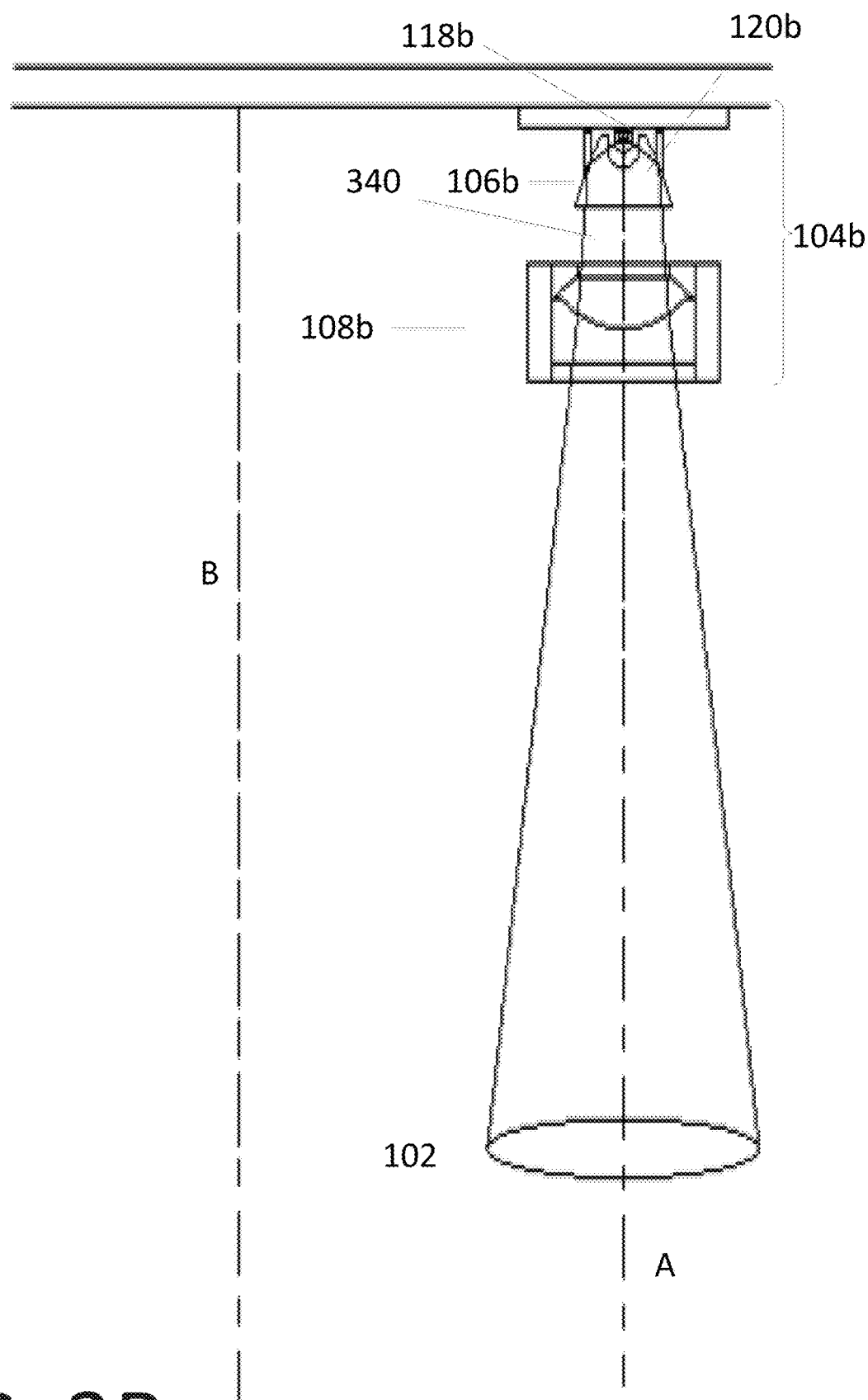

FIG. 3B is similar to FIG. 3A except in FIG. 3B, the liquid lens 108b changes the size of the beam spot. This represents another exemplary manner in which a liquid lens may influence light from a corresponding one of the light emitting cells in a particular luminaire.

Figure 3C:
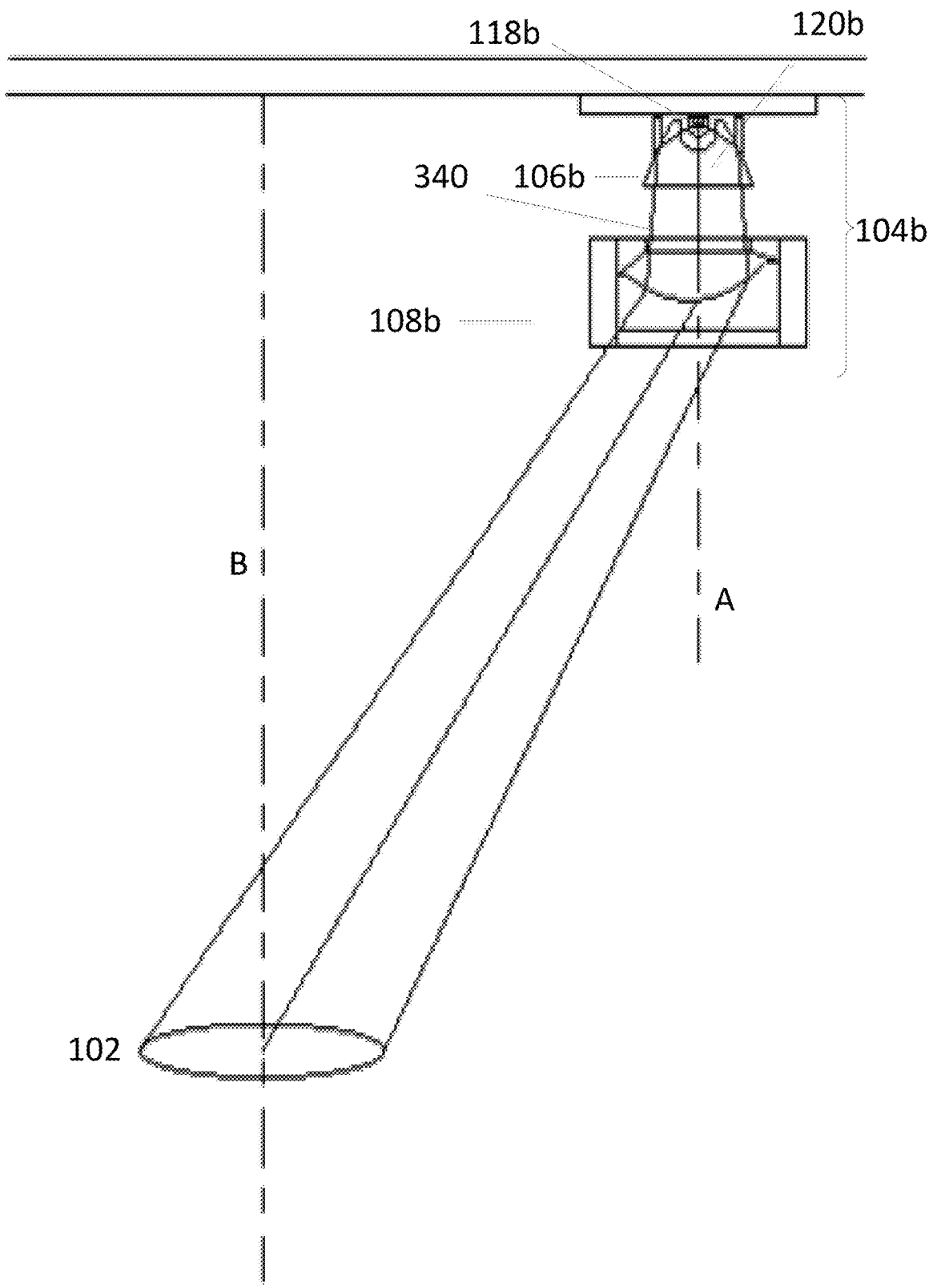

FIG. 3C is similar to FIG. 3A except in FIG. 3C, the liquid lens 108b changes both the direction and size of the beam spot. This represents yet another exemplary manner in which a liquid lens may influence light from a corresponding one of the light emitting cells in a particular luminaire.

In any one luminaire at a given point in time, any one or more of the light emitting cells may behave like the light emitting cell in FIG. 3A, any one or more of the light emitting cells may behave like the light emitting cell in FIG. 3B, and any one or more of the light emitting cells may behave like the light emitting cell in FIG. 3C.

FIGS. 4A and 4B are side views showing an exemplary focus-tunable lens, which in the illustrated implementation is a liquid lens 450, in two operational states.

The liquid lens 408 in the illustrated implementation has a housing that is filled with two fluids such as water 428 and oil 430 that do not readily mix but that form an interface surface 422 therebetween. The housing has two transparent windows on opposite sides of the fluid container—one inlet window 432 that allows light (e.g., from a collimated light source) to enter the fluid container so that the light can pass through (and be influenced by) the oil-water interface surface 422, and—an outlet window 434 that allows the influenced light to exit the fluid container. The liquid lens 408 also has electrode(s) 436 that may be coupled to an electric power source (not shown in FIGS. 4A and 4B). The electrode(s) 436 are configured such that, when energized, an electromagnetic field is produced that influences and/or can be varied to influence contour of the oil-water interface surface 422a. Changes in the contour of the oil-water interface surface 422a can affect the direction, beam size, intensity, etc. of light that passes through the liquid lens 408.

The operational state of the liquid lens 408 as represented in FIG. 4A is one in which light from a collimated light source enters the liquid lens 408 and is influenced by the oil-water interface surface 422 to create a focused beam at the outlet of the liquid lens 408. The focused beam at the outlet of the liquid lens 408 in FIG. 4A is substantially symmetrical about a centerline of the liquid lens along the optical path of the light passing through the liquid lens.

The operational state of the liquid lens 408 represented in FIG. 4B is one in which light from the collimated light source enters the liquid lens 408 and is influenced by the oil-water interface surface 422 to create a focused beam at the outlet of the liquid lens 408. The focused beam at the outlet of the liquid lens 408 in FIG. 4B is angled relative to (and not symmetrical about) the centerline of the liquid lens along the optical path of the light passing through the liquid lens.

In a typical implementation, each respective one of the liquid lenses (e.g., 108a, 108b in FIG. 1) in a particular luminaire (e.g., 100 in FIG. 1) would be able to switch between the operational states represented in FIGS. 4A and 4B and many other operational states (e.g., with different bend angles, and/or with different degree of focus, for example, being applied to the light).

FIGS. 5A and 5B are side views showing an alternative example of a focus-tunable lens, in two operational states.

The focus-tunable lens 508 in the illustrated implementation is a shape-changing lens based on a combination of optical fluids 510 and a polymer membrane 512. The lens 508 has a container 514, which may be filled with the optical fluid 510 and sealed off with a thin, elastic polymer membrane 512. A circular ring (e.g., lens shaper 516) is configured to push onto the center of the membrane to shape the tunable lens. The deflection of the membrane and with that the radius of the lens can be changed by pushing the ring towards the membrane or by exerting a pressure to the outer part of the membrane or by pumping liquid into or out of the container.

In a typical implementation of a luminaire that includes focus-tunable lenses such as those shown in FIGS. 5A and 5B, the luminaire may include a movable element (e.g., a mechanical arm, or a pump or the like), powered by a small motor, for example, configured to push the ring towards the membrane or exert a pressure on an outer part of the membrane or to pump liquid into or out of the container.

The operational state of the focus-tunable lens 508 as represented in FIG. 5A is one in which light from a light source enters the focus-tunable lens 508 and is influenced by the fluid interface surface to focus the light just a bit at the outlet of the focus-tunable lens 508. The focused beam at the outlet of the focus-tunable lens 508 in FIG. 5A is substantially symmetrical about a centerline of the focus-tunable lens along the optical path of the light passing through the focus-tunable lens.

The operational state of the focus-tunable lens 508 represented in FIG. 5B is one in which light from the light source enters the focus-tunable lens 508 and is influenced by the fluid interface surface to focus the light more than happens when the focus-tunable lens is in the FIG. 5A configuration. The focused beam at the outlet of the focus-tunable lens 508 in FIG. 5B is substantially symmetrical about a centerline of the focus-tunable lens along the optical path of the light passing through the focus-tunable lens.

In a typical implementation, each respective one of the liquid lenses (e.g., 108a, 108b in FIG. 1) in a particular luminaire (e.g., 100 in FIG. 1) would be able to switch between the operational states represented in FIGS. 5A and 5B and many other operational states (e.g., with different degrees of focus, for example, being applied to the light).

Figure 6B:
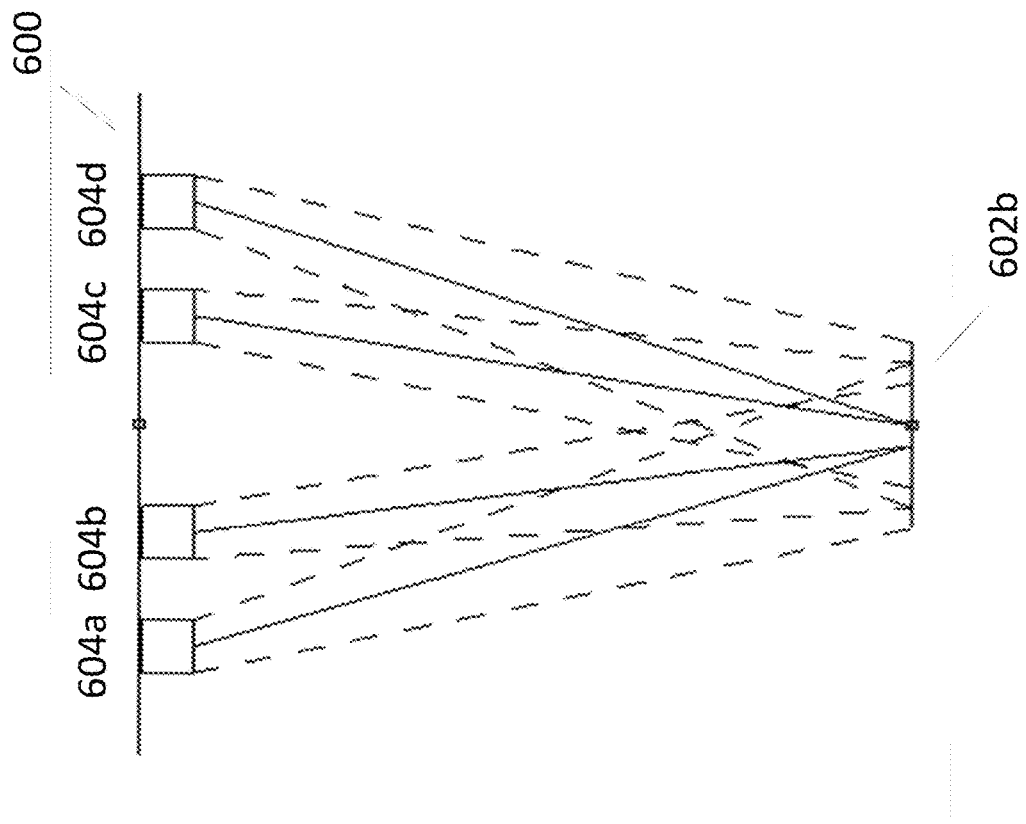
FIGS. 6A and 6B are schematic side view representations of an exemplary luminaire that includes four independently adjustable light emitting cells, each of which is substantially similar to the light emitting cells shown in FIG. 1.
Figure 6A:
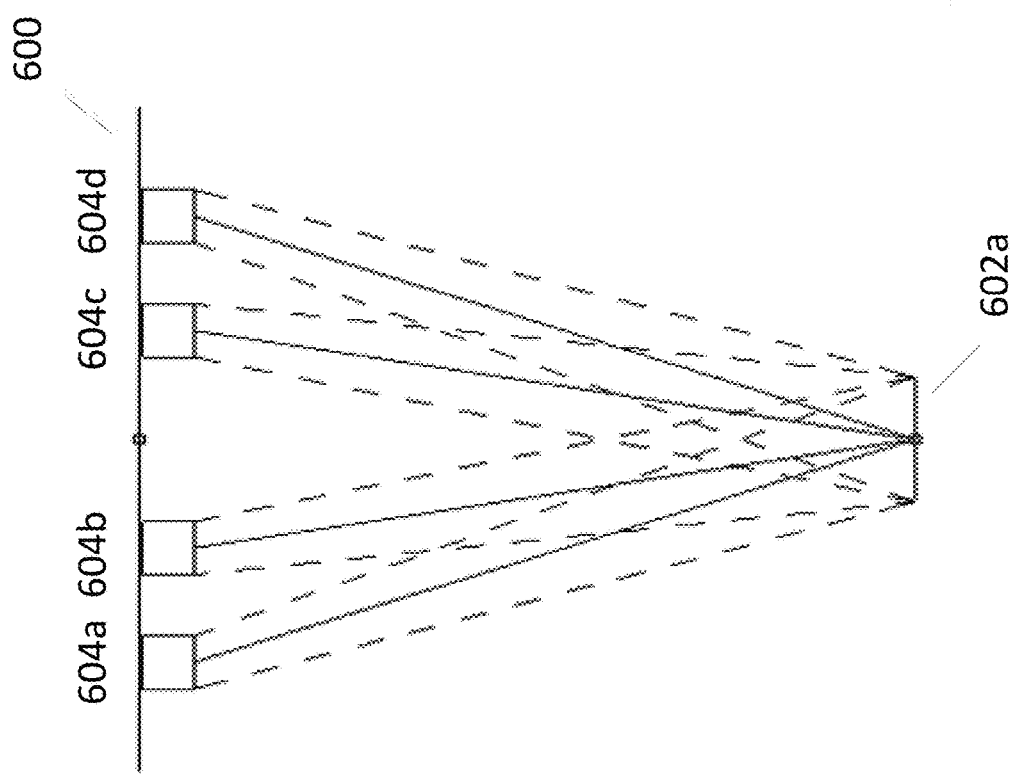

FIGS. 6A and 6B are schematic side view representations of an exemplary luminaire 600 that includes four independently adjustable light emitting cells (604a, 604b, 604c, 604d), each of which is substantially similar to the light emitting cells in FIG. 1.

These images collectively provide one relatively simple example of how a luminaire 600 with independently adjustable light emitting cells (604a, 604b, 604c, 604d) can adjust the light that the luminaire 600 is delivering to a particular site. More particularly, the light beams from the light emitting cells (604a, 604b, 604c, 604d) of the luminaire 600 in FIG. 6A are focused on approximately the same spot. In contrast, the light beams from the light emitting cells (604a, 604b, 604c, 604d) of the luminaire 600 in FIG. 6B are more spread out. Therefore, the light being delivered to site 602a in FIG. 6A might have an overall higher brightness than the light being delivered to site 602b in FIG. 6B, but the light being delivered to site 602b in FIG. 6B covers a larger surface than the light being delivered to site 602a in FIG. 6A.

Figure 7A:
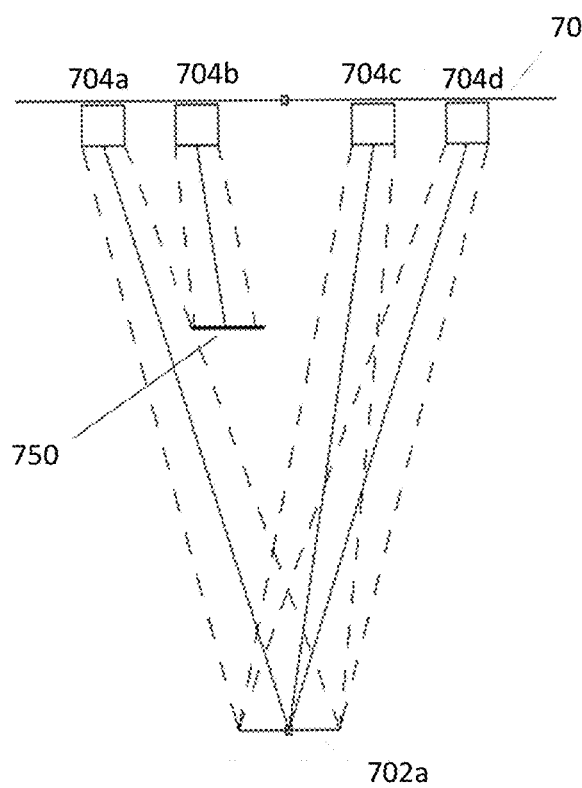
FIGS. 7A and 7B are schematic side view representations of an exemplary luminaire that includes four independently adjustable light emitting cells, each of which is substantially similar to the light emitting cells in FIG. 1, and a physical object between the luminaire and the surface below that is intended to be illuminated by the luminaire.
Figure 7B:
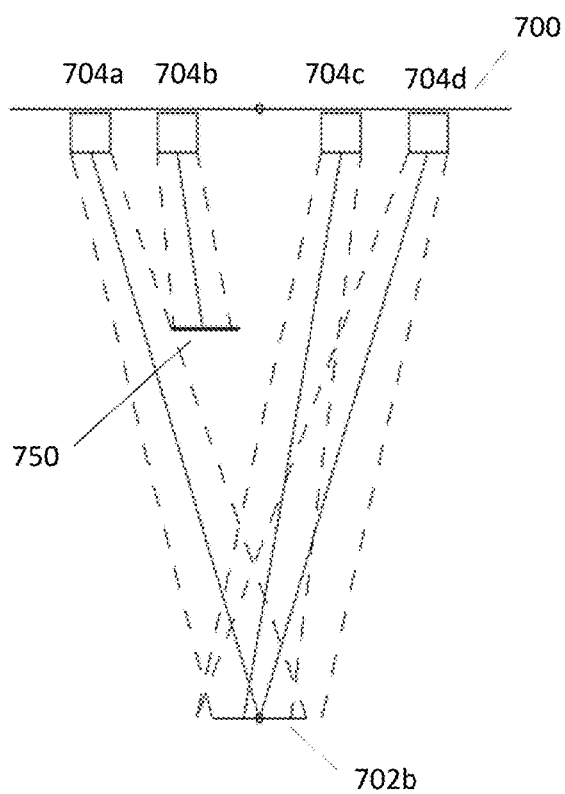

FIGS. 7A and 7B are schematic side view representations of an exemplary luminaire 700 that includes four independently adjustable light emitting cells (704a, 704b, 704c, 704d), each of which may be substantially similar to the light emitting cells in FIG. 1.

Also shown is a physical object 750 (e.g., the hand of a surgeon) between the luminaire 700 and the surface below that is intended to be illuminated by the luminaire 700. Notably, the physical object 750 is positioned relative to the luminaire in such a manner that it blocks at least some of the light from light emitting cell 704b from reaching the surface below—to at least potentially produce a shadow on the surface where the blocked light is prevented from reaching. These images collectively provide one relatively simple example of how a luminaire 700 with independently adjustable light emitting cells (704a, 704b, 704c, 704d) can adjust the light that the luminaire 700 is delivering to a particular site to compensate for (reduce or eliminate) shadows. More particularly, in the illustrated figure, the light beams from light emitting cells 704a, 704c, and 704d of the luminaire 700 change their respective configurations from FIG. 7A (where the shadow from object 750 would be fairly prominent) to their respective configurations in FIG. 7B (where extra light is being diverted into the shadow area from light emitting cells 704a, 704c, and 704d to ameliorate the shadow). Therefore, the shadow is compensated for and the light being delivered to site 702b in FIG. 7B may be more uniform and shadow-free than in FIG. 7A. This shadow compensation can be further improved by increasing light intensity from cells 704a, 704c, 704d through the controller.

Control of individual light emitting cells in a particular HUD may be manual or automatic.

If control is manual, a human user (e.g., a physician, surgeon, dentist, nurse, dental assistant, etc.) might have a hand-operable controller that he or she can manipulate to change the behavior of each independently controllable light emitting cell.

In the hospital environments (e.g., surgical rooms) and other similar locations, however, sterilization can be critical. For a medical luminaire in those kinds of spaces, if human are required to maneuver the luminaire to adjust the light being delivered below, then all the contact/touching areas on the luminaire may need to be disinfected. This concern/issue can be minimized or avoided by providing a luminaire that can be controlled automatically (e.g., without having to physically contact the luminaire or a manual controller) during certain periods of time (e.g., surgical procedures). In a typical implementation, this may be accomplished by using one or more sensors or cameras and an automatic controller, whereby the sensor(s) or camera(s) detect features of a light field along with a target distance, obstacle locations, etc., sends this information to a computer-based controller for processing, the computer-based controller determines any adjustments to light emitting cells inside luminaire that should be performed, and sends one or more signals to the light emitting cells to cause those adjustments to occur. Thus hands-free automatic control can be achieved.

Figure 8:
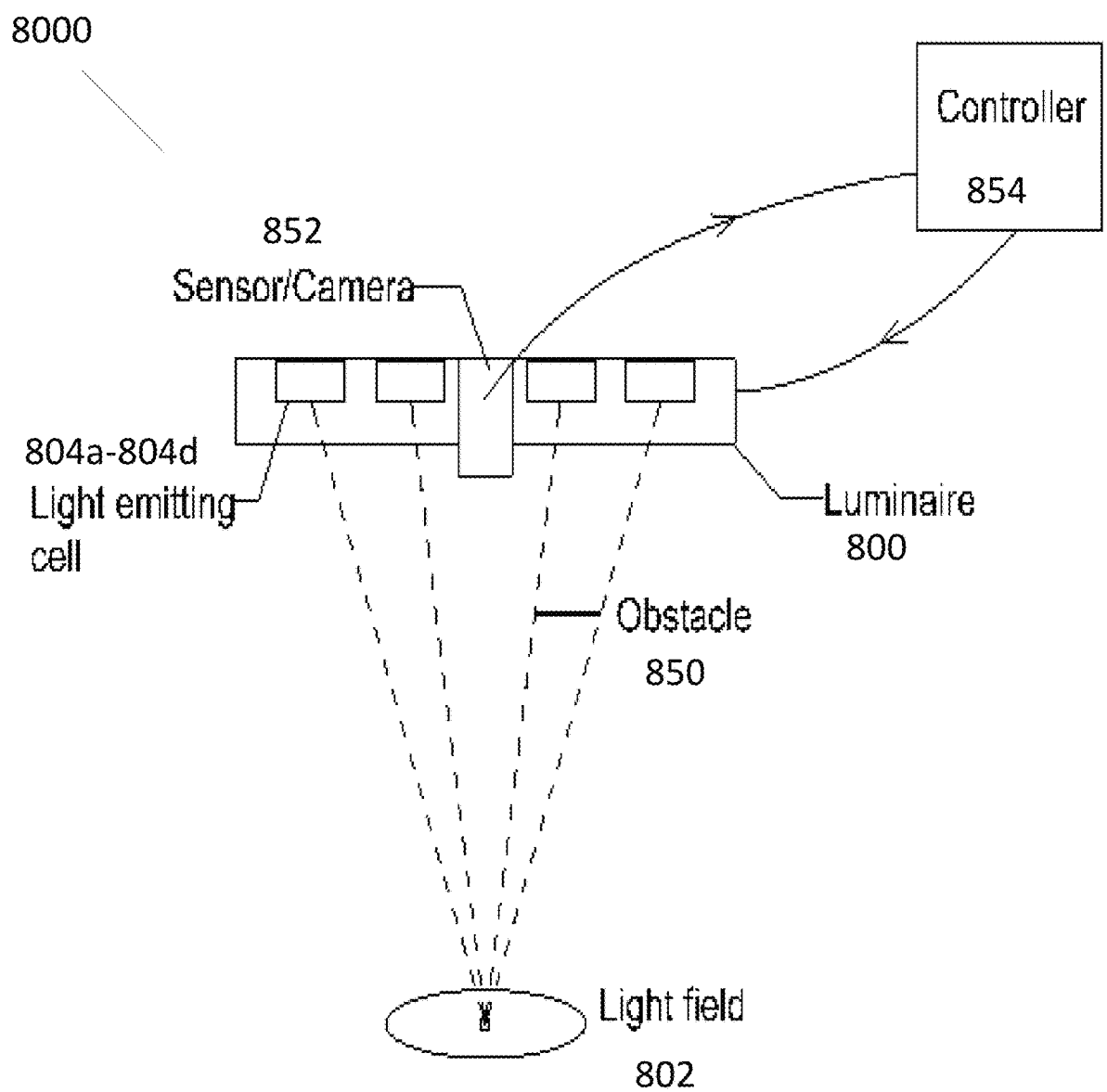
FIG. 8 is a cross-sectional, schematic side view of an exemplary system that includes a luminaire, one or more sensors and/or cameras, and an automatic controller.

FIG. 8 is a cross-sectional, schematic side view of just such a system 8000. More particularly, in the illustrated implementation, the system 800 includes a luminaire 800, one or more sensors and/or cameras 852, and an automatic controller 854.

The luminaire 800 includes a plurality of light emitting cells 804a, 804b, 804c, 804d and each light emitting cell has a light source, and a liquid lens associated with the light source. Each respective one of the light emitting cells 804a, 804b, 804c, 804d in the luminaire 800 is independently controllable relative to other light emitting cells. During operation, the sensor(s) or camera(s) 852 detect one or more of: features of the light field 802 (including, for example, shadows that may be produced by physical objects, such as 850), a target distance (e.g., a height of luminaire), obstacle 850 locations, etc., and sends this information to the computer-based controller 854 for processing. The computer-based controller 854 determines any adjustments that might need to be made (or should be made) to the light emitting cells 804a, 804b, 804c, 804d inside the luminaire 800. The computer-based controller 854 then sends one or more signals to appropriate light emitting cells to cause those adjustments to occur.

In this regard, generally speaking, the sensor(s) or camera(s) 852 may be configured to sense a physical object between the luminaire 800 and a site that is to be illuminated by the luminaire 800 (e.g., light field 802), and the controller 854 may be configured to cause a change in the fluid surface of the liquid lenses (in the light emitting cells 804a, 804b, 804c, 804d) in one or more of the liquid lenses in response to a corresponding signal from the sensor(s) or camera(s) 852. In some implementations, the resulting changes may reduce a shadow that would otherwise be produced at the site by the physical object.

The sensor and/or camera can be any one of a variety of possible devices. In one exemplary implementation, it is a 3D color camera, which is deployed to detect light level, color quality, obstacle location and target location. So the light field can be actively adjusted to provide the most appropriate assistance in regards to the task at hand.

Figure 9:
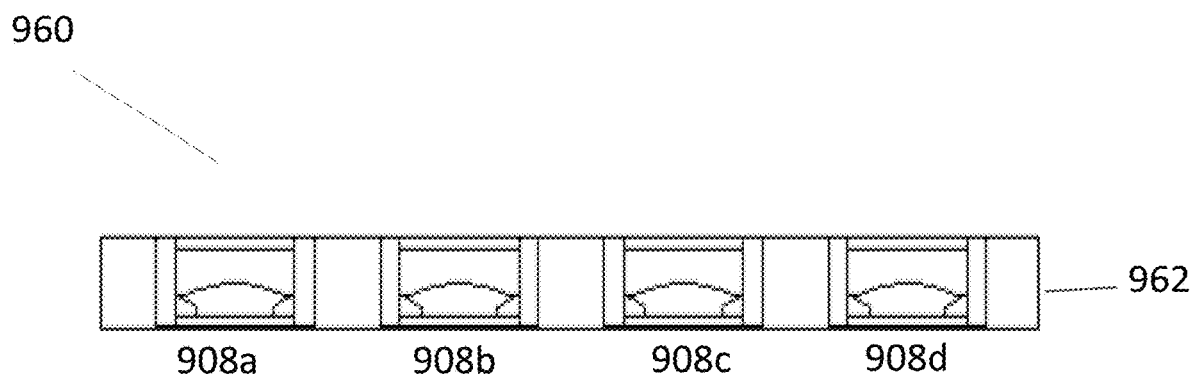
FIG. 9 is a cross-sectional, schematic, side view of an exemplary focus-tunable lens (e.g., liquid lens) module that includes multiple (four) liquid lenses in a single housing.

FIG. 9 is a cross-sectional, schematic side view of an exemplary focus-tunable lens (e.g., liquid lens) module 960 that includes multiple (four) liquid lenses 908a, 908b, 908c, 908d in a single housing 962. Some luminaires may include a focus-tunable lens module such as this, instead of multiple individual focus-tunable lenses. In various implementations, the housing 962 may be a mere physically supporting substrate for the liquid lenses 908a, 908b, 908c, 908d. In other implementations, the housing 962 may also include electrical conductors (e.g., traces, vias, etc.) for delivering electrical energy to each respective liquid lens 908a, 908b, 908c, 908d, independently. In some implementations, the module 960, with the integral liquid lenses, may form a single piece cover for a luminaire.

Figure 10:
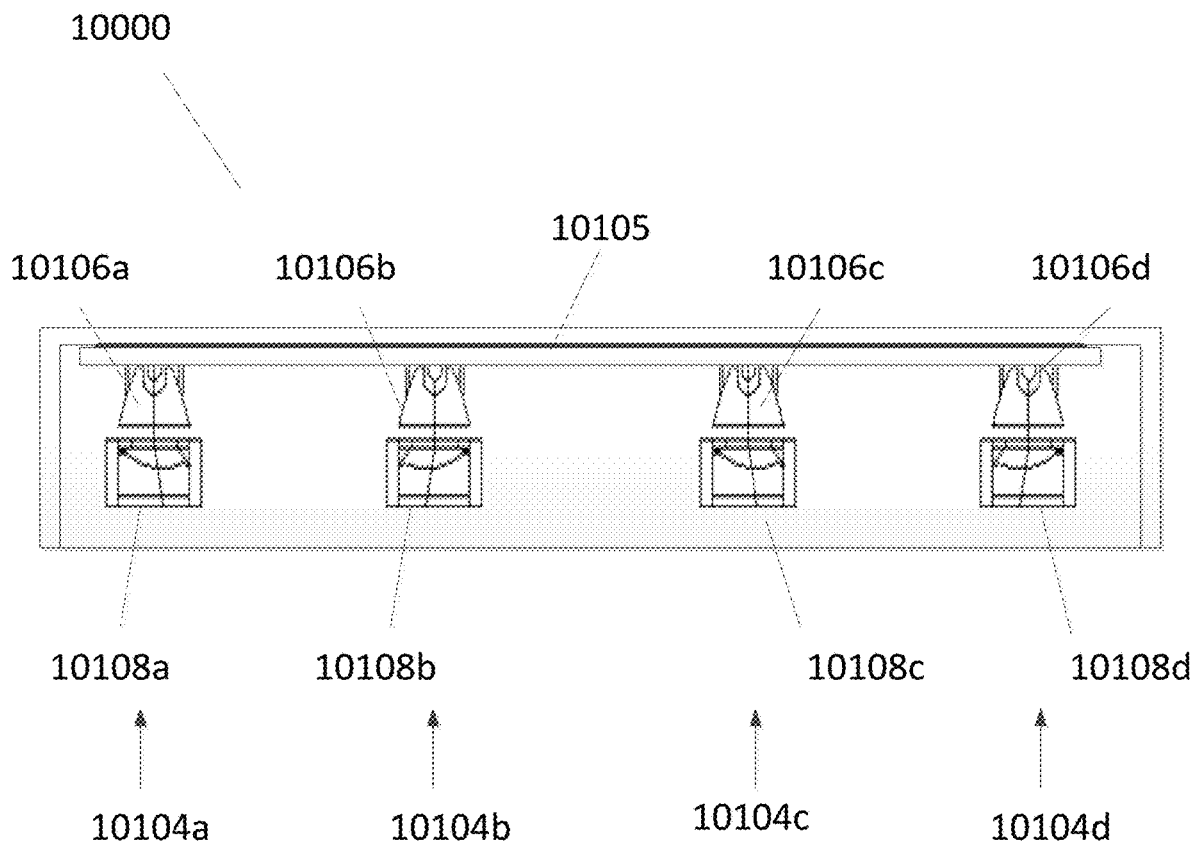
FIG. 10 is a cross-sectional, schematic, side view of an exemplary luminaire with multiple (four are shown) light emitting cells on a single printed circuit board.

FIG. 10 is a cross-sectional, schematic, side view of a luminaire 10000 with multiple (four are shown) light emitting cells (e.g., 10104a, 10104b, 10104c, 10104d). There is one single printed circuit board 10105, and each light emitting cell (e.g., 10104a, 10104b, 10104c, 10104d) includes a light source 10106a, 10106b, 10106c, 10106d physically coupled to that single printed circuit board 10105 and an focus-tunable lens (e.g., a liquid lens 10108a, 10108b, 10108c, 10108d) associated with each light source 10106a, 10106b, 10106c, 10106d (and supported directly or indirectly by the single printed circuit board 10105. In some implementations, a luminaire may include multiple printed circuit boards with at least some of the light emitting cells are on each respective one of the printed circuit boards.

A number of embodiments of the invention have been described. Nevertheless, it will be understood that various modifications may be made without departing from the spirit and scope of the invention.

For example, the size, shape, position, and/or arrangement of each respective component in the luminaires disclosed herein can vary considerably. More particularly, for example, the size, shape, position, and/or arrangement of light emitting cells can vary considerably from luminaire to luminaire. Likewise, the size, shape, position, and/or arrangement of the housing can vary considerably from luminaire to luminaire. Moreover, the number of light emitting cells in a particular luminaire can vary considerably. Additionally, the control can vary considerably from luminaire to luminaire.

According to some of the disclosed implementations, there is one and only one light emitting cell coupled to each printed circuit board. Of course, in some implementations, there can be two or more light emitting cells coupled to any one (or more) of the printed circuit boards in a luminaire. Additionally, the focus-tunable optical component can be virtually any kind of independently-controllable optical component whose focus can be adjusted.

The controller in a various implementations can take on any one of a variety of different configurations. In a typical implementation that might include a hand-operated controller, for example, the hand-operated controller may include buttons or other elements that can be manipulated to control each specific one or more of the focus-tunable elements independently.

In some implementations, the mounting surface for the light emitting cells in a luminaire may not be flat, but instead, may be angled. In one specific implementation, the mounting surface may be angled in a manner that generally tilts the optical axis ("A") of one or more (or all of) the light emitting cells in a luminaire toward, or away from, the axis ("B") of the overall luminaire, or in any other direction.

In some implementations, the light source may be thermally (and, optionally, physically) coupled to a heat sink.

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination. In some implementations, for example, a luminaire (e.g., a medical luminaire) may have one and only one light emitting cell (e.g., with a light source and a focus-tunable (e.g., liquid) lens).

Similarly, while operations may be depicted and described herein as occurring in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

The concepts disclosed herein can be applied to virtually any kind of luminaire (e.g., device that produces or provides light to a particular area).

It should be understood that relative terminology used herein, such as "upper", "lower", "above", "below", "front", "rear," etc. is solely for the purposes of clarity and is not intended to limit the scope of what is described here to require particular positions and/or orientations. Accordingly, such relative terminology should not be construed to limit the scope of the present application.

Additionally, the term substantially, and similar words, such as substantial, are used herein. Unless otherwise indicated, substantially, and similar words, should be construed broadly to mean completely or almost completely or very nearly, or to within normal manufacturing tolerances as would be recognized by a person having ordinary skill in the art.

Other implementations are within the scope of the claims.

What is claimed is:

1. A system comprising:
   a luminaire comprising:
      a plurality of light emitting cells, wherein each of the light emitting cells comprises:
         a light source; and
         a focus-tunable liquid lens associated with the light source,
      wherein each respective one of the light emitting cells in the luminaire is independently controllable relative to every other one of the plurality of light emitting cells,
   a controller coupled to the light emitting cells; and
   a sensor coupled to the controller, wherein the sensor is configured to sense a presence of a physical object between the luminaire and a site that is to be illuminated by the luminaire,
   wherein the controller is configured to control each respective one of the plurality of light emitting cells independently of every other one of the plurality of light emitting cells, and
   wherein the controller is configured such that, in response to receiving a signal from the sensor indicating the presence of the physical object between the luminaire and the site to be illuminated, the controller controls a particular one of the light emitting cells in the luminaire to cause a change in a liquid surface in the focus-tunable liquid lens for the particular light emitting cell, wherein the change in the liquid surface produces a change in a direction of light being produced by the particular light emitting cell to reduce a shadow at the illumination site from the physical object.

2. The system of claim 1, wherein each focus-tunable liquid lens comprises:
   one or more fluids in a housing configured such that light from the light source can pass through the liquid surface, which is defined by the one or more fluids; and
   a means for varying the liquid surface,
   wherein changing the liquid surface further results in a change in beam size, and/or intensity of light that exits the focus-tunable liquid lens after passing through the liquid surface.

3. The system of claim 1, further comprising:
   a housing that defines a substantially flat mounting surface for the light emitting cells,
   wherein the light emitting cells are coupled to the substantially flat mounting surface such that an axis of each light emitting cell is substantially parallel to an axis of the luminaire.

4. The system of claim 1, wherein each of the light emitting cells further comprises one or more optics configured to direct light from the light source to the focus-tunable liquid lens.

5. The system of claim 1, wherein controlling each respective light emitting cell comprises:
   causing a change in the liquid surface of the focus-tunable liquid lens in that light emitting cell; and/or
   causing a change in voltage or current to be delivered to the light source of that light emitting cell.

6. The system of claim 1, further comprising a plurality of printed circuit boards, wherein each of the printed circuit boards has one or more of the light emitting cells coupled thereto.

7. The system of claim 1, further comprising:
   a substrate to physically support the focus-tunable liquid lenses; and
   electrical conductors at the substrate to deliver electrical energy to each of the focus-tunable liquid lenses.

8. A method of delivering light to a site to be illuminated, the method comprising:
   providing a luminaire that comprises:
      a plurality of light emitting cells, wherein each of the light emitting cells comprises:
         a light source; and
         a focus-tunable liquid lens associated with the light source,
      wherein each respective one of the light emitting cells is independently controllable relative to every other one of the plurality of light emitting cells; and
   controlling each respective one of the plurality of light emitting cells in the apparatus independently from every other one of the lighting emitting cells in the apparatus to adjust a light beam produced by the apparatus,
   wherein controlling a particular one of the light emitting cells comprises:
      controlling, in response to receiving a signal from a sensor indicating a presence of a physical object between the luminaire and the site to be illuminated, a particular one of the light emitting cells in the luminaire to cause a change in a liquid surface in the focus-tunable liquid lens for the particular light emitting cell, wherein the change in the liquid surface produces a change in a direction of light being produced by the particular light emitting cell to reduce a shadow at the illumination site from the physical object.

9. The system of claim 1, further comprising:
   wherein the controller is an automatic controller,
   wherein the sensor detects features of a light field along with a target distance, and obstacle locations; sends the detected features of the light field along with the target distance, and obstacle locations information to the automatic controller for processing, and
   wherein the automatic controller determines any adjustments to the light emitting cells that should be performed, and sends one or more signals to the light emitting cells to cause those adjustments to occur.

10. A system comprising:
    a luminaire comprising:
       a housing that defines a substantially flat mounting surface;
       a plurality of light emitting cells, wherein each of the light emitting cells comprises:
          a light source; and
          a liquid lens associated with the light source,
          one or more optics configured to direct light from the light source to the liquid lens,
       wherein each respective one of the light emitting cells in the lumninaire is coupled to the substantially flat mounting surface such that an axis of each light emitting cell is substantially parallel to an axis of the luminaire,
wherein each respective one of the light emitting cells in the luminaire is independently controllable relative to every other one of the plurality of light emitting cells, a controller coupled to the light emitting cells; and a sensor coupled to the controller, wherein the sensor is configured to sense a presence of a physical object between the luminaire and a site that is to be illuminated by the luminaire, wherein the controller is configured to control each respective one of the plurality of light emitting cells independently of every other one of the plurality of light emitting cells, and wherein the controller is configured such that, in response to receiving a signal from the sensor indicating the presence of the physical object between the luminaire and the site to be illuminated, the controller controls a particular one of the light emitting cells in the luminaire to cause a change in a liquid surface in the liquid lens for the particular light emitting cell, wherein the change in the liquid surface produces a change in a direction of light being produced by the particular light emitting cell to reduce a shadow at the illumination site from the physical object.

* * * * *